(12) United States Patent
Jinno et al.

(10) Patent No.: US 7,211,189 B2
(45) Date of Patent: May 1, 2007

(54) SEPARATION COLUMN FROM CHROMATOGRAPHY, MEDIUM FOR SOLID PHASE EXTRACTION AND SAMPLE INJECTION SYSTEM FOR CHROMATOGRAPHY

(75) Inventors: Kiyokatsu Jinno, 38-1-104, Aza-Nakahara, Yayoi-Cho, Toyohashi-Shi Aichi-ken (JP); Yoshihiro Saito, Toyohashi (JP); Tsutomu Takeichi, Toyohashi (JP); Hiroo Wada, Kyoto (JP)

(73) Assignees: Shinwa Chemical Industries, Ltd., Kyoto-Shi (JP); Kiyokatsu Jinno, Toyohashi-Shi (JP)

( * ) Notice: Subject to any disclaimer, the term of this patent is extended or adjusted under 35 U.S.C. 154(b) by 55 days.

(21) Appl. No.: 10/873,206

(22) Filed: Jun. 23, 2004

(65) Prior Publication Data

US 2005/0000874 A1    Jan. 6, 2005

Related U.S. Application Data

(62) Division of application No. 09/984,714, filed on Oct. 31, 2001, now Pat. No. 6,780,314.

(30) Foreign Application Priority Data

Nov. 1, 2000   (JP)   ............................. 2000-334960

(51) Int. Cl.
    *B01D 15/08*   (2006.01)
(52) U.S. Cl. ............................. 210/198.2; 210/502.1; 210/500.23; 210/635; 210/656
(58) Field of Classification Search ................ 210/635, 210/656, 198.2, 502.1, 500.23
    See application file for complete search history.

(56) References Cited

U.S. PATENT DOCUMENTS 4,077,906 A   3/1978   Hughes (Continued)

FOREIGN PATENT DOCUMENTS

JP           63-70080         5/1988

OTHER PUBLICATIONS

Kiyokatsu Jinno, et al., "Cellulose Acetate Fiber as Stationary Phase in Capillary Electrochromatography", J. High Resol. Chromatogr., vol. 21, No. 11, 1998, pp. 617-619, XP-002263279.

(Continued)

*Primary Examiner*—Ernest G. Therkorn
(74) *Attorney, Agent, or Firm*—Oblon, Spivak, McClelland, Maier & Neustadt, P.C.

(57) ABSTRACT

A separation column for chromatography or a medium for solid phase extraction, which comprises a hollow capillary and a collected body packed in the hollow capillary and serving as a stationary phase, the collected body comprising long fibers having an adsorbing ability selective towards a target solute and arranged in the axial direction of the capillary, and a sample injection system which comprises the foregoing hollow capillary incorporated into a loop of a valve or a passage connecting two valves, the valve(s) being used as an injector for the chromatography. The use of the polymeric long fibers, which have chemical structures specially designed so that they can specifically interact with a target substance (a solute or an analyte) to be analyzed, permits the selective or preferential extraction and/or concentration of the solute.

16 Claims, 14 Drawing Sheets

U.S. PATENT DOCUMENTS

| | | |
|---|---|---|
| 4,225,442 A | 9/1980 | Tremblay et al. |
| 4,375,163 A | 3/1983 | Yang |
| 4,455,187 A | 6/1984 | von Blucher et al. |
| 4,483,773 A | 11/1984 | Yang |
| 4,657,742 A | 4/1987 | Beaver |
| 4,834,877 A | 5/1989 | Peters |
| 4,891,137 A | 1/1990 | Nohl |
| 4,957,620 A | 9/1990 | Cussler |
| 5,160,627 A | 11/1992 | Cussler |
| 5,286,449 A | 2/1994 | Kuroda |
| 5,482,773 A | 1/1996 | Bair |
| 5,578,204 A | 11/1996 | Bartholmes |
| 5,683,916 A | 11/1997 | Goffe |
| 5,691,206 A | 11/1997 | Pawliszyn |
| 5,702,610 A | 12/1997 | Hagen et al. |
| 5,702,616 A | 12/1997 | Degen et al. |
| 5,868,936 A | 2/1999 | Ofsthun |
| 5,911,883 A * | 6/1999 | Anderson ................ 210/679 |
| 5,954,962 A | 9/1999 | Adiletta et al. |
| 6,022,478 A | 2/2000 | Baurmeister |
| 6,214,232 B1 | 4/2001 | Baurmeister |
| 6,270,674 B1 | 8/2001 | Baurmeister |
| 6,475,340 B1 | 11/2002 | Carlson et al. |
| 6,492,183 B1 | 12/2002 | Perman et al. |

OTHER PUBLICATIONS

Yoshihiro Saito, et al. "Fiber-in-Tube Solid-Phase Microextraction: A Fibrous Rigid-Rod Heterocyclic Polymer as the Extraction Medium", Fresenius J. of Anal. Chem., vol. 368, 2000, pp. 641-643, XP02263278.

Y. Kiso, et al., "Liquid Chromatography in a Capillary Packed with Fibrous Cellulose Acetate", Journal of High Resol. Chromatography & Chromatography Communications, vol. 9, 1996, pp. 763-764, XP 009022031.

Yoshihiro Saito, et al. "Direct Coupling of Microcolumn Liquid Chromatography with in-Tube Solid-Phase Microextraction for the Analysis of Antidepressant Drugs", The Royal Society of Chemistry, vol. 125, Mar. 29, 2000, pp. 807-809, XP009022050.

PTO Translation 2003-1748 of Japan Patent 63-70080, pp. 1-2, Feb. 10, 2003.

* cited by examiner

FIG. 3
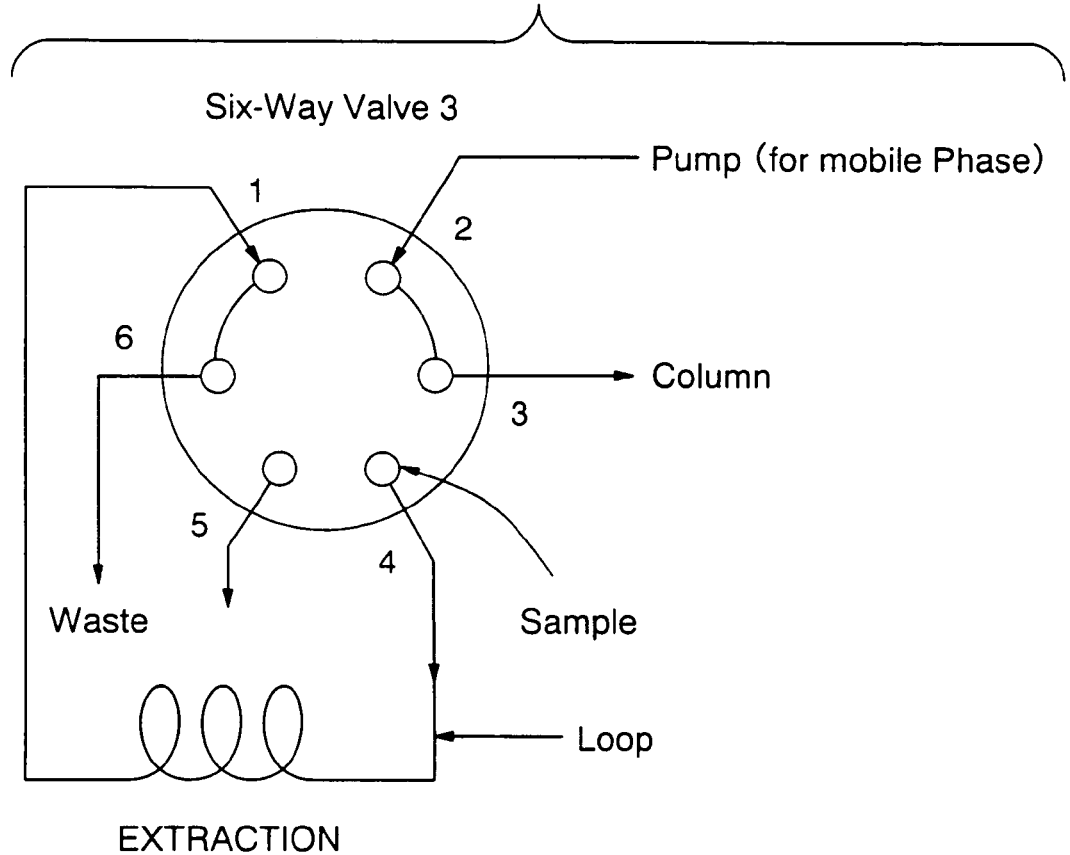
EXTRACTION
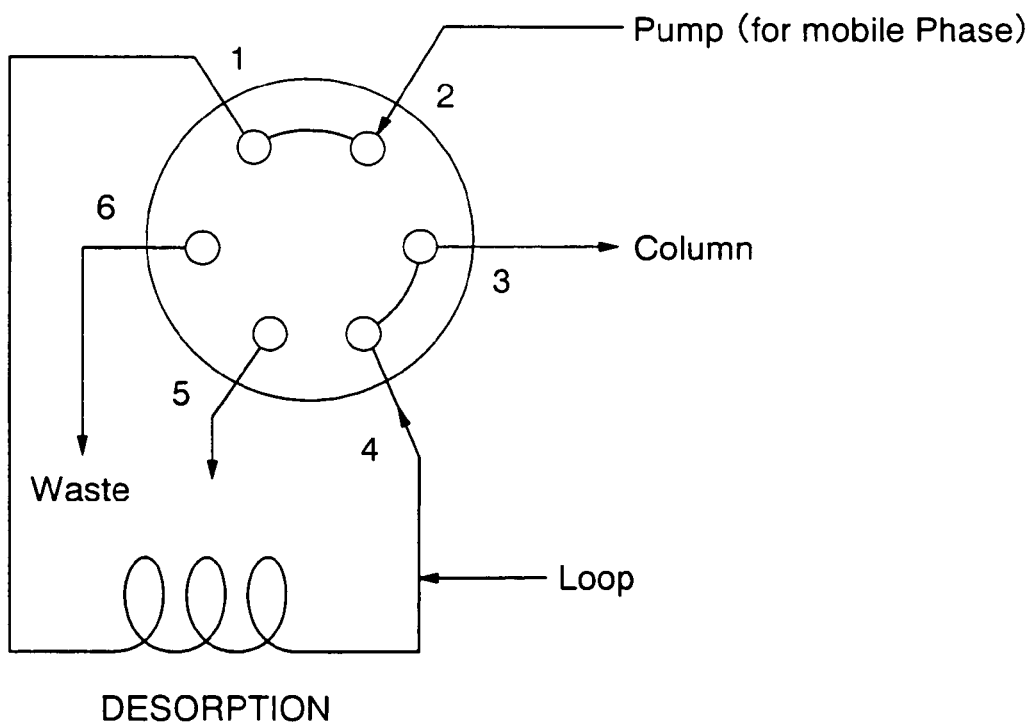
DESORPTION

SEPARATION COLUMN FROM CHROMATOGRAPHY, MEDIUM FOR SOLID PHASE EXTRACTION AND SAMPLE INJECTION SYSTEM FOR CHROMATOGRAPHY

This application is a Divisional application of U.S. Ser. No. 09/984,714, filed on Oct. 31, 2001, now U.S. Pat. No. 6,780,314.

BACKGROUND OF THE INVENTION

The present invention relates to a separation column for chromatography, a medium for solid phase extraction and a sample injection system for chromatography.

The solid phase microextraction (hereafter referred to as "SPME" or "solid phase extraction") technique is the most powerful technique for the preliminary concentration of a sample in the analysis of organic compounds present in an aqueous sample using gas chromatography (GC). The SPME technique requires simpler operations and the use of a smaller amount of a solvent as compared with the conventional solvent extraction techniques and therefore, a wide variety of applications of the SPME/GC technique have been proposed. If a fussed silica fiber for use in the SPME technique is immersed in a sample solution, a substance or a compound to be analyzed (analyte) is extracted in a polymer coating present on the fiber. Subsequently, this fiber is introduced into a gas chromatograph through the injection port thereof, and then heated to thus desorb the analyte by the action of the heat. In contrast to the foregoing successful examples, there have been reported only a few attempts to combine the SPME technique with, for instance, the liquid chromatography (LC) technique or an electrokinetic separation technique for the analysis of a non-volatile compound. This is because the difficulty in the operations of the desorption of an analyte and the complicated mechanism of the on-line interface.

Recently, there has been developed another SPME technique by Pawliszyn et al. and more specifically, an in-tube SPME technique in which an SPME device can directly be connected to an LC separation device without using any interface device. This method makes use of an open tube GC-hollow capillary column as an extraction medium. In this case, if a sample solution (for instance, an aqueous solution) is passed through the capillary column using a microflow pump, an analyte present in the aqueous solution is extracted into a polymer coating within the hollow capillary. The analyte (or a solute) thus extracted can likewise be desorbed from the polymer coating by passing a small amount of an organic solvent through the hollow capillary. Thus, this method does not use any desorption device required for sending the extracted solute to a separation device. Therefore, this method permits the elimination of difficult or complicated operations and/or processes and the considerable reduction of the organic solvent required for the desorption of the analyte.

The inventors of this invention have adopted a wire-in-tube structure as an extraction hollow capillary for the analysis of a tricyclic antidepressant present in the human urine sample. This technique permits the reduction of the inner volume of the extraction hollow capillary tube by inserting a stainless steel wire into the hollow capillary, while remaining unchanged the surface area of the coating, which will come in contact with a sample solution. This constitution (or structure) would permit further improvement of the concentration effect as compared with the conventional in-tube type SPME technique. Moreover, this structure would suggest that an on-line wire-in-tube type SPME/LC device can be used for the high speed analysis of a variety of organic compounds present in the matrix of biological and environmental samples with high probability.

On the other hand, the analysis of low concentration phthalates present in the matrix of an aqueous sample is considered to be one of the most important subjects due to its estrogenic action. There have been investigated the quantitative analysis and the functions of phthalates as an endocrine function-disturbing substance, but there has still been desired for the development of an effective and rapid extraction-concentration technique for the practical analysis of an environmental water sample, which does not require the consumption of a large amount of a solvent.

Moreover, Japanese Un-Examined Utility Model Publication No. Sho 63-70080 discloses a separation column for chromatography, which comprises a hollow capillary and a stationary phase packed in the hollow capillary and comprising a collected body, which comprises cellulose acetate long fibers having an adsorbing ability selective towards a solute and arranged along the axial direction of the hollow capillary. This column employs cellulose acetate fibers as the long fibers and therefore, it can be used as a separation column for liquid chromatography, but it is difficult to use the same for gas chromatography. In addition, this publication never suggests that this column can be used as a medium for solid phase extraction, which is effective for the concentration of a liquid sample.

SUMMARY OF THE INVENTION

Accordingly, it is a first object of the present invention to provide a separation column for chromatography excellent in the separation ability.

It is a second object of the present invention to provide a medium for solid phase extraction, which is effective for the concentration of fluid samples, in particular, liquid samples.

It is a third object of the present invention to provide a sample injection system for chromatography.

The present invention provides a separation column for chromatography, which comprises a hollow capillary and a collected body packed in the hollow capillary and serving as a stationary phase, the collected body comprising long fibers having an adsorbing ability selective towards a target solute and arranged along the axial direction of the capillary. More specifically, the present invention provides a separation column for, in particular, liquid chromatography (hereafter also referred to as "LC"), gas chromatography (hereafter also referred to as "GC") or capillary electrochromatography (hereafter also referred to as "CEC").

According to another aspect of the present invention, there is provided a medium for solid phase extraction, which comprises a hollow capillary and a collected body packed in the hollow capillary and serving as a stationary phase, the collected body comprising long fibers having an adsorbing ability selective towards a target solute and arranged along the axial direction of the capillary.

According to a third aspect of the present invention, there is provided a sample injection system for use in chromatography, which is characterized in that a hollow capillary is incorporated into a loop of a valve or into a passage connecting two valves, the valve(s) being used as an injector of the chromatography and the hollow capillary being packed with a collected body as a stationary phase, which comprises long fibers having an adsorbing ability selective towards a target solute present in a sample or a specimen and is arranged along the axial direction of the hollow capillary.

BRIEF DESCRIPTION OF THE DRAWINGS

FIG. 3 is a diagram showing a second embodiment of the sample injection system of the present invention, which makes use of only one six-way valve and a method for using the same.

Mobile Phase A: Methanol/Water=50/50 (v/v)
Mobile Phase B: Methanol/Water=40/60 (v/v)

Figure 16:
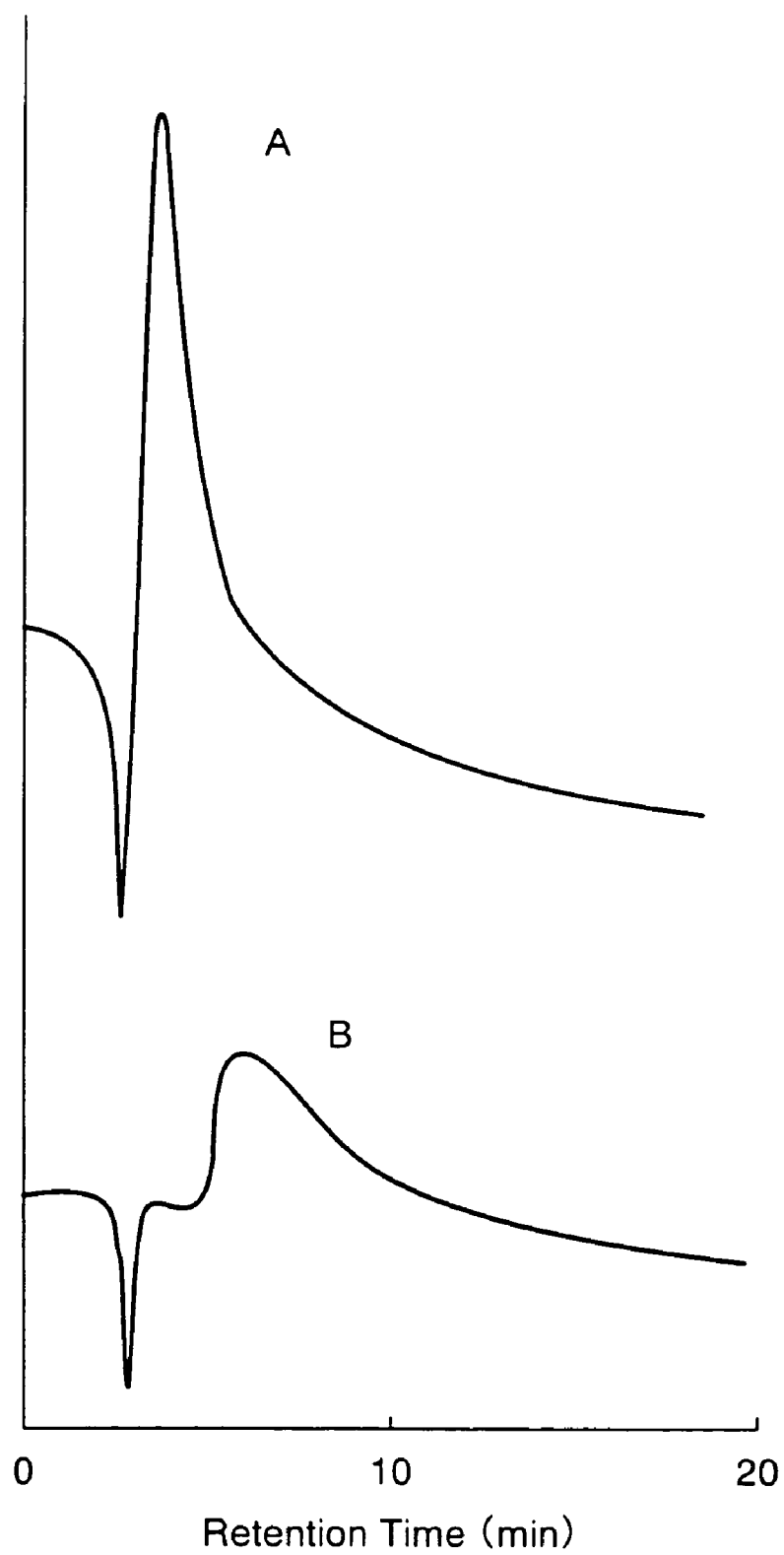

FIG. 16 is a chromatogram showing the results obtained by analyzing pyrene by the liquid chromatography technique using a hollow capillary column packed with ZYLON fibers (HM Type).

Mobile Phase A: Methanol/Water=80/20 (v/v)
Mobile Phase B: Methanol/Water=70/30 (v/v)

DESCRIPTION OF THE PREFERRED EMBODIMENTS

The separation column for chromatography according to the present invention comprises a hollow capillary and a stationary phase packed in the hollow capillary and comprising a collected body, which comprises cellulose acetate long fibers having an adsorbing ability selective towards a target solute and arranged in the axial direction of the capillary. Materials for preparing the long fibers used herein may be a variety of materials inasmuch as they have an adsorbing ability selective towards a target solute, but they are desirably selected from the group consisting of high strength polymers, heat-resistant polymers, durable polymers and any combination thereof, while taking into consideration easiness of packing them in the hollow capillary, stability to, for instance, extraction solvents, durability and heat resistance. Specific examples of such polymers are aramid fibers (for instance, PPTA fibers such as Kevlar (registered trademark) and Technora (registered trademark)); completely aromatic polyesters (polyarylates or polyaryl esters) such as Vectran (registered trademark) and Econol (registered trademark); heterocyclic-containing aromatic polymers and other rod-like polymers (for instance, poly (p-phenylene-benzobisthazole) (PBO) such as ZYLON (registered trademark), poly (benzimidazole) (PBI) and poly (benzobisthiazole) (PBT)); polyimides; polyalkylenes such as polyethylene and polypropylene; polyoxyalkylenes such as polyoxymethylene; polyvinyl alcohol; nylons such as nylon-6 and nylon-6,6; polyesters such as polyethylene terephthalate; carbon fibers; cellulose acetate fibers; and any combination of at least two of them.

In the present invention, the long fibers to be packed in the hollow capillary have a diameter preferably ranging from 100 nm to 100 μm and more preferably 500 nm to 15 μm.

The length of the long fiber is not particularly restricted to any specific range, insofar as it is equal to or higher than the length of the hollow capillary, but the length in general range from 1 μm to 100 m and preferably 1 mm to 10 m.

The long fiber may have any cross sectional shape such as a circular, triangular, tetragonal or rectangular, other polygonal, V-shaped, Y-shaped or star-shaped cross section.

When packing the long fiber in the hollow capillary, it is desirable to remove any impurity and/or contaminant adhered to the surface of the fibers or mixed in the fibers during the production of the same and this is accomplished by, for instance, washing with an appropriate solvent or a heat-treatment.

Moreover, to improve the extraction efficiency and the separation efficiency of the fibers, it is also preferred to subject the fibers to a surface treatment (including chemical modification) with a surface-treating agent, for instance, liquids currently used in GC such as silicone oil or polyethylene glycol; or to chemical modification of the surface of the fibers with, for instance, an inactivation agent such as bis(trimethylsilyl) acetamide (BSA) or dimethyldichlorosilane.

The hollow capillary used in the present invention may be prepared from any material selected from the group consisting of fussed silica, glass, plastics, metals, alloys and composite materials, inasmuch as they never interact with a substance to be analyzed (an analyte), an extraction solvent and an elution solvent. The inner diameter of the hollow capillary in general ranges from 500 nm to 600 µm and preferably 1 to 600 µm. On the other hand, the outer diameter thereof may vary depending on the material selected, but in general ranges from 170 to 660 µm and preferably 200 to 660 µm.

The long fibers are packed in the hollow capillary along the longitudinal direction of the latter and the total number of long fibers to be packed in general ranges from 10 to 3000 and preferably 10 to 500. If the total number of the long fibers is small, the surface area of the fiber is small and this leads to insufficient separation efficiency and extraction efficiency when used as a medium for solid phase extraction as will be detailed below. On the other hand, if the total number thereof is large, a problem arises, for instance, a high pressure is required for letting flow a fluid.

These long fibers having the same diameter or different diameters may be used in the present invention. Moreover, the long fibers may or may not be twisted.

The treatments of the long fibers such as washing, heating and/or surface treatments may be carried out before, during or after the packing thereof in the hollow capillary.

The packing of the long fibers into the hollow capillary permits the reduction of the inner volume of the hollow capillary and simultaneously the increase in the surface area of the long fibers used for the separation and/or extraction of a substance to be analyzed.

The separation column for chromatography according to the present invention can be used in, for instance, liquid chromatography (LC), gas chromatography (GC) and capillary electrochromatography (CEC).

The medium for solid phase extraction of the present invention, which comprises a hollow capillary column packed with long fibers, is not frequently used at a high temperature, unlike the separation column for chromatography according to the present invention. Therefore, the long fibers used may have heat resistance lower than that required for the separation column for chromatography and the hollow capillary may likewise have heat resistance and pressure resistance inferior to those required for the separation column for chromatography. The diameter of the long fiber, the length of the hollow capillary, the inner diameter of the hollow capillary and the number of the long fibers to be charged are the same as those used for the separation column for chromatography.

The medium for solid phase extraction according to the present invention, which comprises a hollow capillary column containing long fibers packed therein, is useful in the concentration of a fluid sample, in particular, a liquid sample. For instance, to analyze a trace component (for instance, phthalates) present in an environmental water sample, a liquid sample containing such a trace component is passed through the medium for solid phase extraction in advance to thus concentrate the trace component by extracting (or adsorbing) the same on the surface of the long fibers packed in the hollow capillary. Then the concentrated sample is subjected to an appropriate chromatography technique such as a GC, LC or CEC technique to thus analyze the substance or analyte. It is a matter of course that the separation column for chromatography according to the present invention, which comprises a hollow capillary packed with long fibers and which has been described above, can be used in this stage.

The sample injection system of the present invention will now be detailed below.

Figure 1:
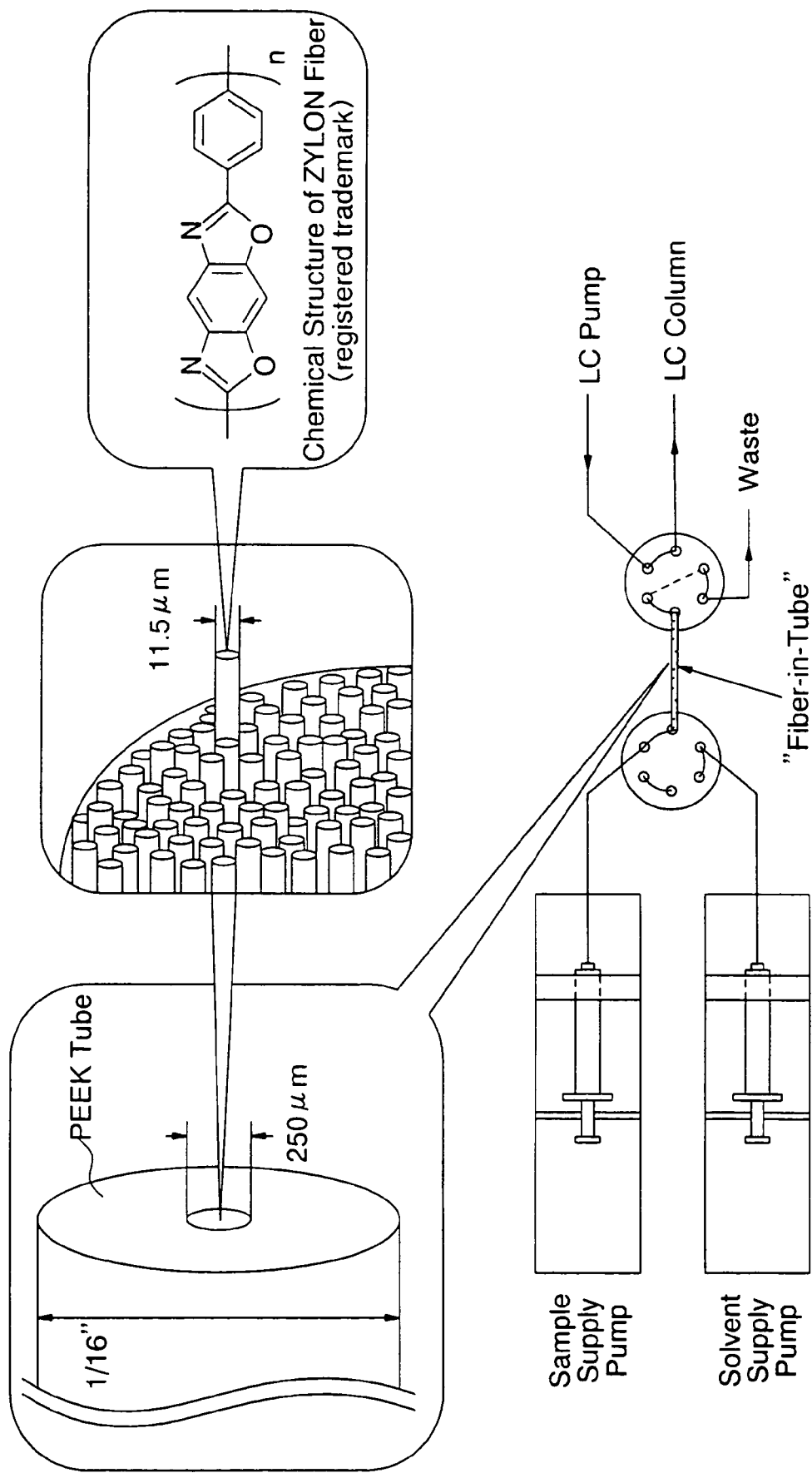
FIG. 1 shows a partial cross sectional view illustrating a medium for solid phase extraction, which comprises a hollow capillary charged with heterocyclic polymer fibers "ZYLON (registered trademark)" and a schematic diagram illustrating a system for injecting, in an LC column, a concentrated sample obtained by concentrating a sample using the foregoing medium for solid phase extraction.

In the sample injection system of the present invention, one or two valves are used and the sample injection system comprises a medium for solid phase extraction consisting of a hollow capillary column packed with long fibers according to the present invention, the medium for solid phase extraction being inserted in the loop of the valve or a passage connecting the two valves, in which the valve(s) are used as an injector. As such valves used as an injector, there have been known four-way valves and six-way valves and they are put on the market. Among these, an analysis system comprising the combination of a sample injection system, in which two six-way valves are used, with an LC chromatograph is schematically shown in FIG. 1.

Figure 2:
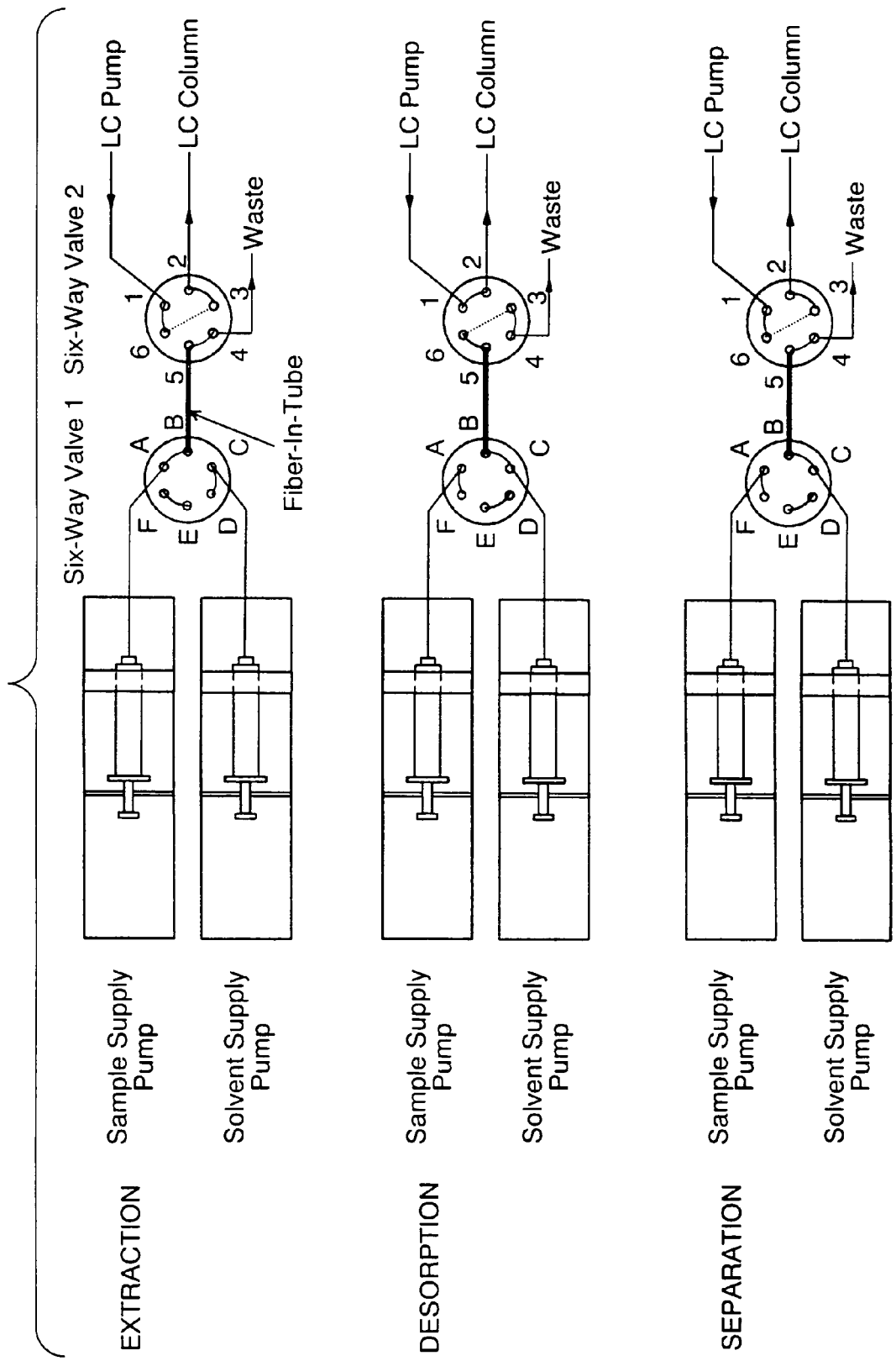
FIG. 2 is a diagram showing a first embodiment of the sample injection system of the present invention, which makes use of two six-way valves and a method for using the same.

A sample injection system, in which two six-way valves are used, according to a first embodiment of the present invention and a method for using the same will hereafter be described with reference to the accompanying drawing (FIG. 2). The two six-way valves are provided with ports A to F and ports 1 to 6, respectively. The port B of the six-way valve 1 on the left hand side of the figure is connected to the port 5 of the six-way valve 2 on the right hand side of the figure through a fiber-in-tube (the hollow capillary column of the present invention). When extracting a sample, the sample is injected, using a pump for sample injection, to the port A of the six-way valve 1 at the first position 1. The sample thus injected is released through the port B, the fiber-in-tube and the port 5 and the port 4 of the six-way valve 2. The target component is adsorbed on the fibers when the sample passes through the fiber-in-tube. At this stage, a mobile phase for chromatography (in this embodiment, an LC mobile phase) is pumped into the port 1 of the six-way valve 2 so that the mobile phase is fed to the column through the port 6, the port 3 and the port 2.

Then we will explain the desorption of the sample thus adsorbed on the fibers. After the completion of the sample injection, the positions of the six-way valves 1 and 2 were switched to the second positions, respectively. Subsequently, if a solvent for desorption is injected to the port C of the six-way valve 1 by the action of a solvent injection (supply) pump, the solvent is released through the port B, the fiber-in-tube and the port 5, the port 6, the port 3 and the port 4 of the six-way valve 2. The component adsorbed on the fibers is desorbed as the solvent passes through the fiber-in-tube.

Then we will hereafter explain the column separation of the sample thus desorbed. If the six-way valve 2 is switched to the first position while maintaining the six-way valve 1 at its second position, the mobile phase for chromatography injected into the port 1 of the six-way valve 2 is fed to the column through the port 6, the port 3 and the port 2 thereof and the solution containing the desorbed component and present between the ports 6 and 3 of the six-way valve 2 is forced out into the column by the action of the mobile phase so that the desorbed component is thus separated.

We will then explain a method for using a sample injection system, which makes use of one six-way valve, as a second embodiment of the present invention with reference to FIG. 3. In this embodiment, the six-way valve 3 is equipped with ports 1 to 6 and the extraction is performed at the first position thereof. A sample is injected into the port 4 and then released through a fiber-in-tube (a hollow capillary column packed with long fibers according to the present invention), the port 6 and the port 5. A mobile phase for column chromatography is pumped to the port 2 and fed to the column through the port 3.

Then if the six-way valve is switched to the second position, the mobile phase fed to the port 2 is transferred to the column through the port 1, the fiber-in-tube, the port 4 and the port 3, the component adsorbed on the fibers of the fiber-in-tube is desorbed by the action of the mobile phase and the solution containing the desorbed component is forced out into the column by the action of the mobile phase so that the desorbed component is thus separated.

This second embodiment employs only one six-way valve and a mobile phase as the desorption solvent. Therefore, this embodiment has such advantages that the constitution (structure) thereof is quite simple as compared with that of the first embodiment, that the amount of a sample required for the analysis can further be reduced and that the use of any particular desorption solvent can be eliminated. It is also possible to further reduce the length of the fiber-in-tube if using an injection valve provided with a rotor available from Rheodyne Company as a six-way valve and providing a gap or a hole for accommodating the fiber-in-tube on or within the rotor.

The sample injection system of the present invention is characterized in that a hollow capillary is equipped with, as a stationary phase, a collected body retained therein, which comprises long fibers having an adsorbing ability selective towards a target solute and arranged within the loop of a valve or the passage connecting two valves along the axial direction of the hollow capillary, the valve(s) being used as injectors. As has been discussed above, the hollow capillary may serve to concentrate a sample. For this reason, the sample injection system of the present invention permits the direct injection of a sample without any pre-treatment of the sample and thus permits the completion of the chromatography operation only by a single operation for injection, while the conventional technique requires multiple steps for pre-treatment of the sample and this results in the contamination and loss of a quite valuable sample. Therefore, it would be easy to automate the operations extending from the collection of a sample to the detection of a target component present therein. In addition, a sample can directly be injected into a detection system and therefore, this sample injection system permits the simplification of the detection and analysis of a trace amount of a sample in the fields of, for instance, the legal medicine (on-site inspection) and field works (such as the environmental investigations and the investigations of air pollution).

The present invention will hereafter be described in more detail with reference to the following Examples, but the present invention is not restricted to these specific Examples at all.

EXAMPLE 1

This Example is herein given for illustrating or explaining the preparation of the medium for solid phase extraction according to the present invention, the concentration of an aqueous sample using the medium and the separation of the concentrated sample by the liquid chromatography. The outline of the connected state of these devices used in this Example and the operations of valves are shown in FIGS. 1 and 2.

Heterocyclic polymer fibers "ZYLON (registered trademark)" (available from Toyobo Co., Ltd.) were cut into something having a length of 10 cm and then packed into a PEEK (polyether ether ketone) tube (inner diameter: 0.25 mm, outer diameter: 1/16" (1.59 mm), available from GL Science Company) along the longitudinal direction thereof to thus give an extraction tube (see FIG. 1). The diameter of each filament constituting the foregoing fiber is about 11.5 $\mu$m and the total number of filaments packed in the PEEK tube is about 280.

As shown in FIG. 2, a six-way valve 2 (Rheodyne Model 7000 Valve available from U.S. Rheodyne Company) was used as an injector (loop volume of 1 $\mu$l (the loop between the port 3 and the port 6 of the six-way valve) and two Microfeeder MF-2 pumps (available from Adzuma Denki Kogyo K.K.) equipped with MS-GAN Microsyringe (available from GL Science Company) were used as a sample supply pump and a solvent supply pump. A sample solution was fed to an extraction tube (a fiber-in-tube) connected to the port B of the six-way valve 1 and the port 5 of the six-way valve 2 through the port A of the six-way valve 1 at a flow rate of 16 $\mu$l/min for 20 minutes. Then the six-way valves 1 and 2 were switched from the first position to the second position and then a desorption solvent (pure methanol) injected through the port C of the six-way valve 1 was passed through the port B of the valve 1, the extraction tube and the port 5, the port 6, the port 3 and the port 4 of the six-way valve 2 at a flow rate of 2 $\mu$l/min for 3.5 minutes. Thereafter, the six-way valve 2 was switched to the first position, a mobile phase was passed through the ports 1, 6, 3 and 2 of the six-way valve 2 by the operation of an LC pump to thus introduce the solution containing the compounds to be analyzed (analyte) present in the loop (the loop between the port 3 and the port 6) into an LC column. This LC device comprises a PU-980 HPLC pump, UV-970 UV-visible light detector (available from JASCO Co., Ltd.) and an Inertsil ODS 2 column (inner diameter: 4.6 mm×250 mm, particle size: 5 $\mu$m, available from GL Science Company).

Data were collected using Borwin Chromatography Data Processing Software (available from Nippon Bunko Co., Ltd.). All of the solvents and reagents used in this Example were those of analytical grades.

A sample of domestic waste water (the effluent released from the primary settling tank of the Toyohashi Municipal Nakajima Waste Water Treatment Facility) was collected as a sample waste water. The waste water was immediately filtered through a filter of glass fibers (GA100, pore size: 0.3 $\mu$m, available from Advantec Company) to give a waste water sample.

These filters were used in the filtration step after sufficiently washing with methanol and pure water.

In this connection, we carried out preliminary experiments, according to the method disclosed in The Analyst, 2000, 125:807–809, to determine the amount of the solvent required for the desorption and the flow rate of the solvent in order to ensure the quantitative supply of the analyte to the injection loop (the loop between the port 3 and the port 6 of the six-way valve) during the desorption step and to prevent any leakage of the analyte out of the loop due to an excess supply of the desorption solvent. In these preliminary experiments, there was not observed any carry-over effect even when the analysis was continuously conducted.

Figure 4:
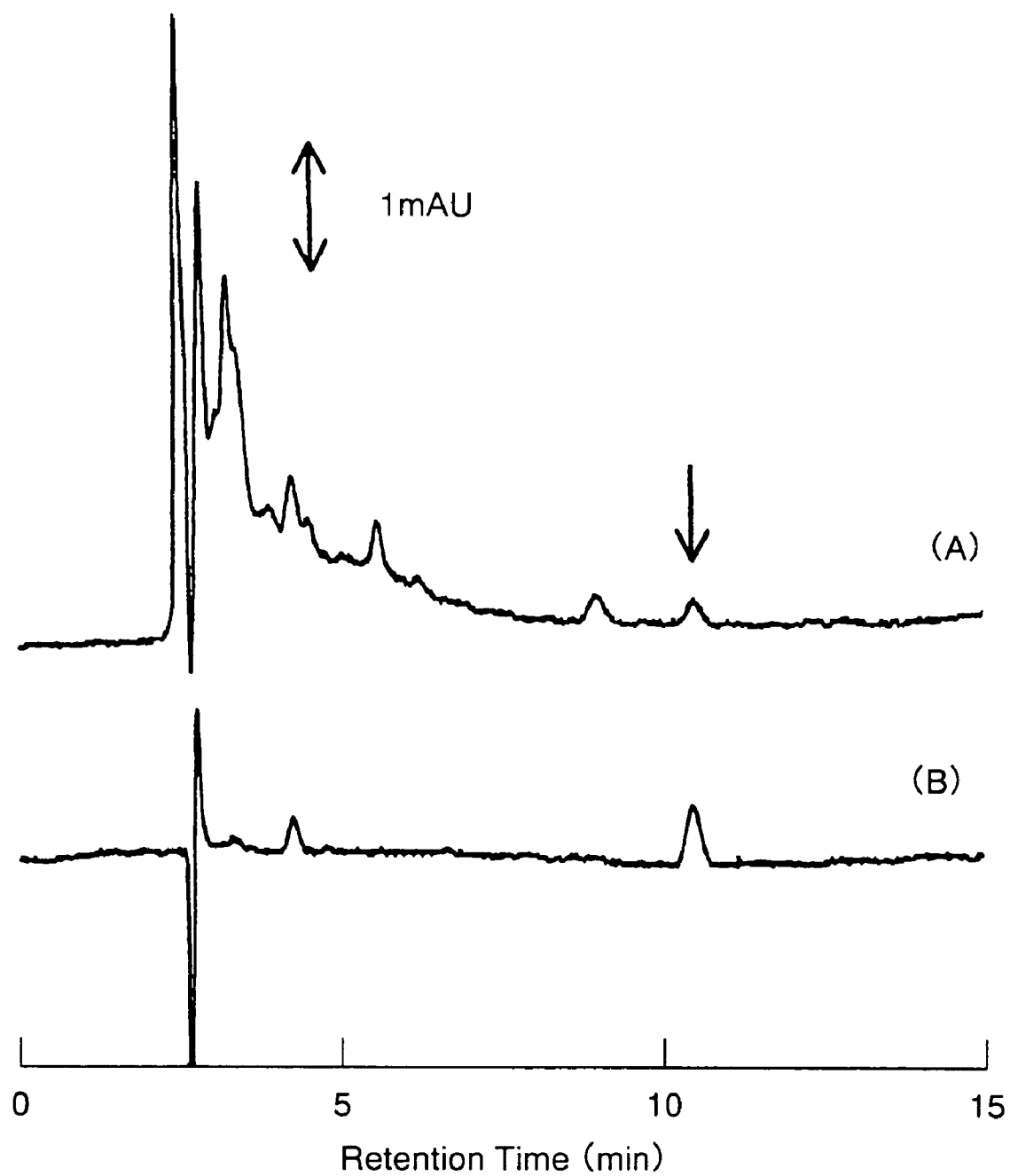
FIG. 4 is a diagram showing the chromatogram obtained when di-n-butyl phthalate present in a water sample is subjected to solid phase extraction and then the extracted phthalate is analyzed by the liquid chromatography.

A typical chromatogram obtained by analyzing di-n-butyl phthalate present in the water sample is shown in FIG. 4. In FIG. 4, (A) represents the waste water sample and (B) represents a reference solution of di-n-butyl phthalate (concentration: 1 ng/ml). When the sample was preliminarily concentrated by the fiber-in-tube SPME technique, there was observed a peak ascribed to di-n-butyl phthalate. This peak was identified by a UV-visible spectrometer. The peak area was determined and compared with that observed for the reference sample (solution) and as a result, the original di-n-butyl phthalate concentration of the waste water was found to be 0.40 ng/ml. As shown in FIG. 4, there was not observed any peak, which interfered with the determination of the concentration of di-n-butyl phthalate. The preliminary concentration factor for di-n-butyl phthalate was calculated as a ratio of the peak area observed for the sample obtained using the fiber-in-tube SPME preliminary concentration to that observed for the sample free of any preliminary concentration (in other words, the peak area obtained by the direct injection of the waste water sample). When the sample was not subjected to any preliminary concentration, there was not any detectable peak at all and therefore, the direct injection was conducted using a reference sample having a concentration of 200 ng/ml. The estimated preliminary concentration factor for di-n-butyl phthalate was found to be about 160. The fibrous extraction medium used herein has a high preliminary concentration factor with respect to di-n-butyl phthalate and therefore, the medium can be applied to a variety of compounds present in the matrix of an aqueous sample.

EXAMPLE 2

This Example is herein provided for illustrating the concentration of an aqueous sample using the medium for solid phase extraction according to the present invention and the separation of the concentrated sample by the liquid chromatography. More specifically, in this Example, there are provided results obtained by the liquid chromatographic analysis of di-n-butyl phthalate present in an aqueous sample preliminarily concentrated by the fiber-in-tube SPME technique. The conditions used for the SPME concentration used in this Example are as follows:
SPME Tube: A PEEK tube (inner diameter: 0.250 mm×24 mm) packed with ZYLON fibers;
Flow Rate and Time of Extraction: 16 μl/min×30 minutes;
Flow Rate and Time of Desorption: 2 μl/min×4 minutes;
Desorption Solvent: Methanol;
Conditions for LC: Column: Develosil ODS-5 (Nomura Chemical) (inner diameter: 0.53 mm×200 mm);
Mobile Phase: Methanol/Water=90/10 (v/v), 4 μl/min;
Amount of Sample Injected: 1 μl; and
Detection: UV (254 nm).

Figure 5:
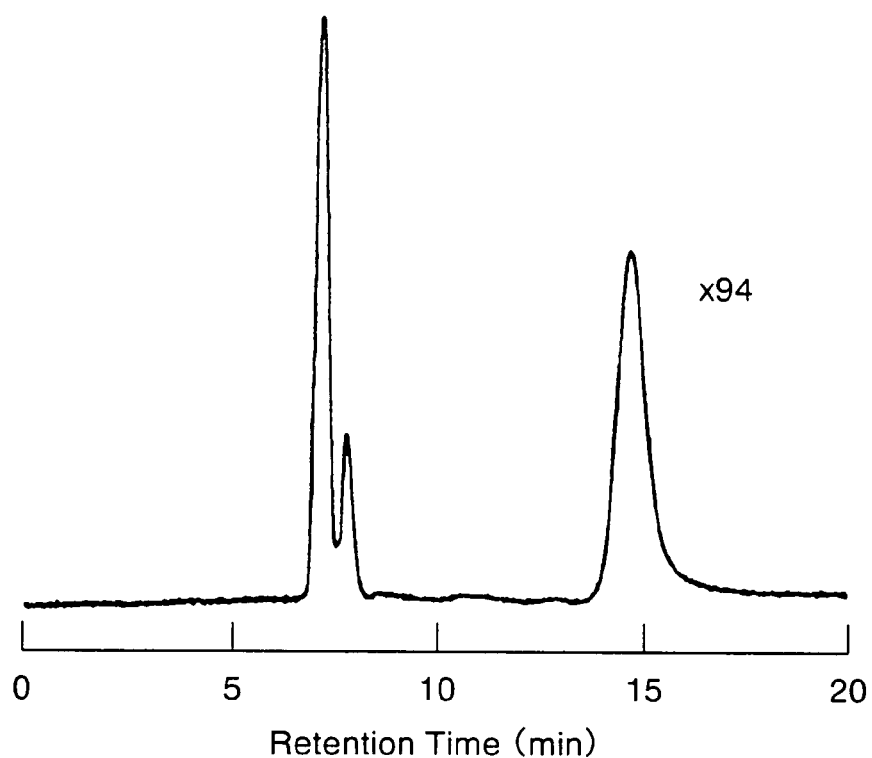
FIG. 5 is a diagram showing the chromatogram obtained when di-n-butyl phthalate present in a water sample is subjected to solid phase extraction and then the extracted phthalate is analyzed by the liquid chromatography.

The chromatogram thus obtained is shown in FIG. 5. In FIG. 5, "×94" means the concentration factor.

EXAMPLE 3

This Example is provided for illustrating an example in which three kinds of n-alkyl p-hydroxybenzoates (common name: parabenes) are separated by the CEC (capillary electrochromatography) technique using the separation column for chromatography (a column packed with ZYLON fibers) according to the present invention. The conditions used for the separation are as follows:
Inner Diameter: 0.2 mm×500 mm; Effective Length: 50 mm;
Mobile Phase: 2.5 mM Tris-HCl Buffer Solution (pH 8.0);
Detection: UV (254 nm);
Applied Voltage: a) 15 kV; b) 10 kV; c) 5 kV.

Figure 6:
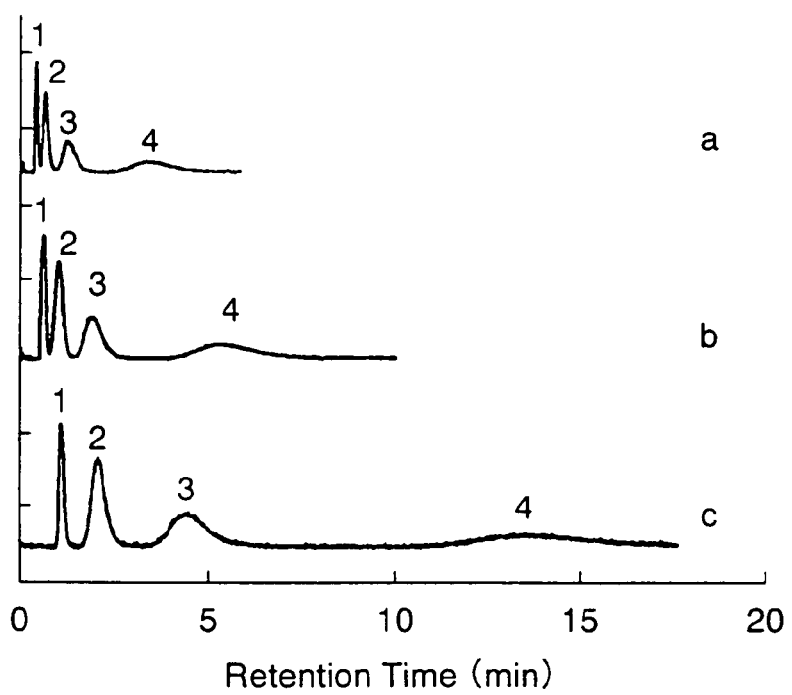
FIG. 6 is a chromatogram showing the results obtained by separating three kinds of n-alkyl p-hydroxybenzoates by the CEC (capillary electrochromatography) technique using a column packed with ZYLON fibers.

The chromatogram thus obtained is shown in FIG. 6. In this figure, the peaks 1 to 4 are assigned to thiourea, ethyl p-hydroxybenzoate, n-propyl p-hydroxybenzoate and n-butyl p-hydroxybenzoate, respectively.

EXAMPLE 4

This Example is herein given for illustrating an example in which four kinds of dialkyl phthalates are separated by the CEC (capillary electrochromatography) technique using the separation column for chromatography (a column packed with ZYLON fibers) according to the present invention. The conditions used for the separation are as follows:
Inner Diameter: 0.2 mm×500 mm; Effective Length: 50 mm;
Mobile Phase: Methanol/Water/50 mM Tris-HCl Buffer Solution (pH 8.2);
Detection: UV (230 nm);
Applied Voltage: 10 kV.

Figure 7:
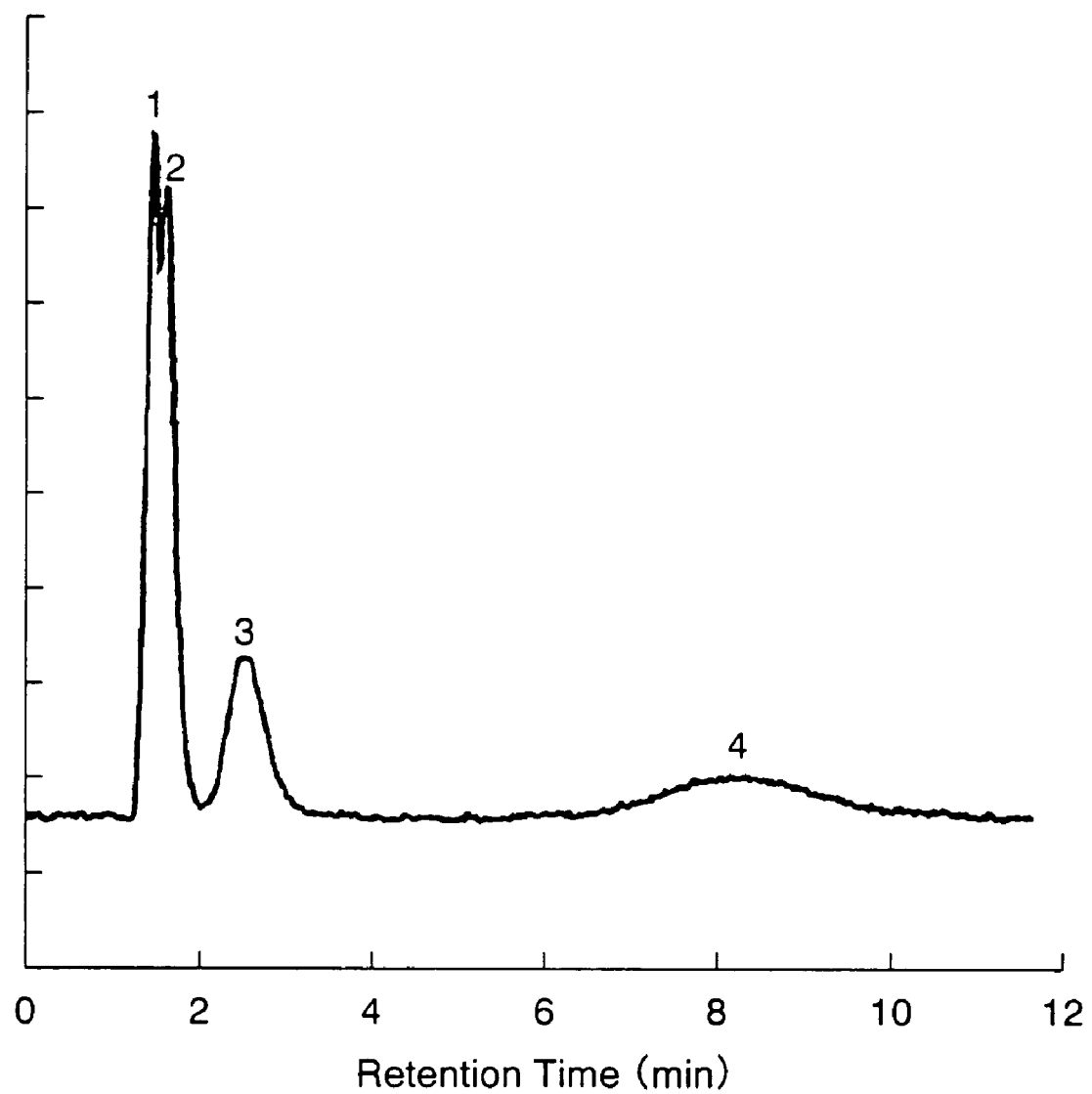
FIG. 7 is a chromatogram showing the results obtained by separating four kinds of di-n-alkyl phthalates by the CEC (capillary electrochromatography) technique using a column packed with ZYLON fibers.

The chromatogram thus obtained is shown in FIG. 7. In this figure, the peaks 1 to 4 are assigned to dimethyl phthalate, diethyl phthalate, di-n-propyl phthalate and di-n-butyl phthalate, respectively.

EXAMPLE 5

This Example is herein given for illustrating an example in which n-alkanes (having 10 to 19 carbon atoms) are separated by the GC (gas chromatography) technique using the separation column for chromatography (a column packed with ZYLON fibers (about 580 to 590 filaments)) according to the present invention. The conditions used for the separation are as follows:
Inner Diameter: 0.53 mm×715 mm;
Column Temperature Program: Raising the temperature at a rate of 10° C./min from 60° C. (5 minutes) to 200° C. (20 minutes);
Injector: splitless (250° C.);
Detection: FID (250° C.);
Column Head Pressure: 200 kPa.

Figure 8:
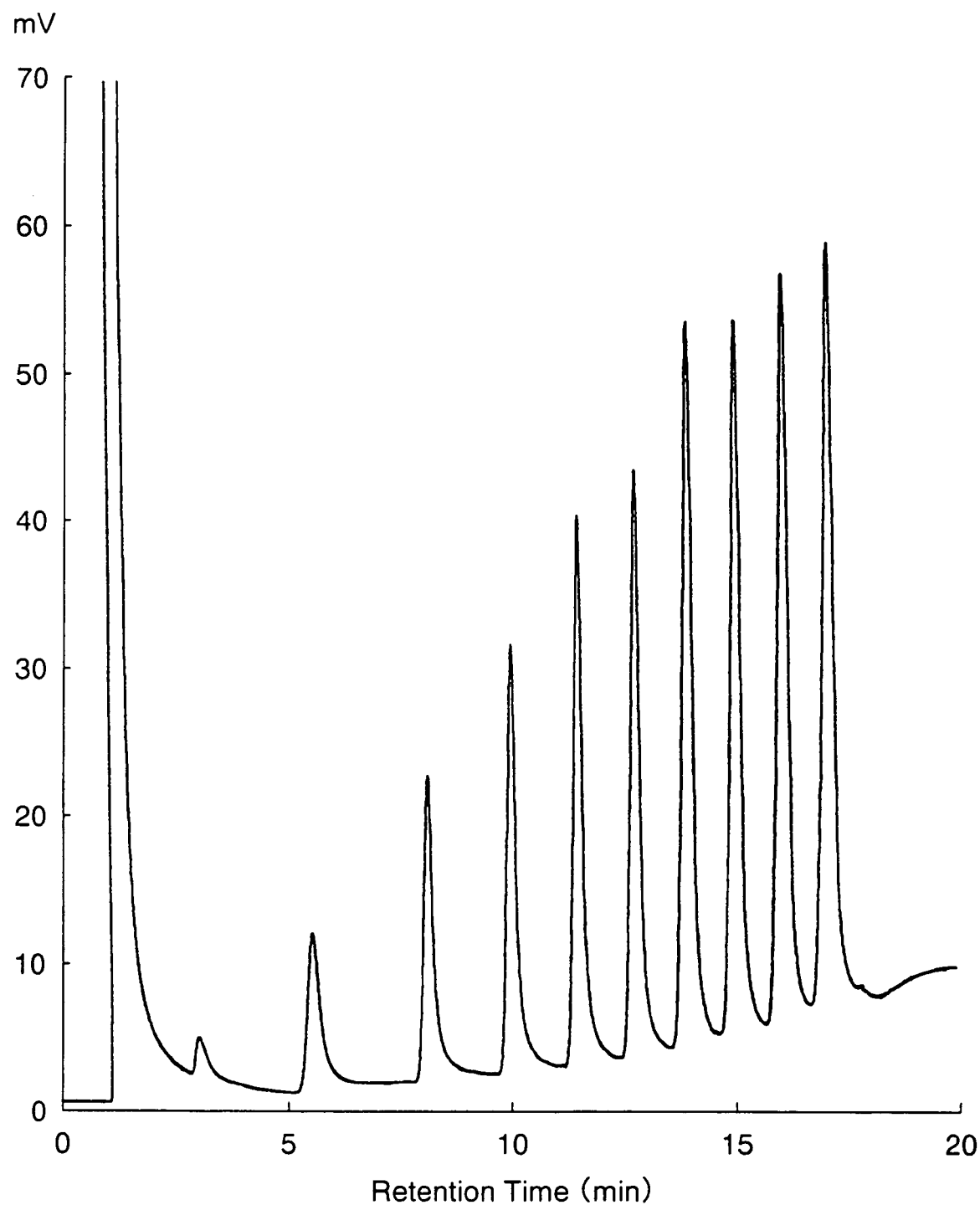
FIG. 8 is a chromatogram showing the results obtained by separating n-alkanes (having 10 to 19 carbon atoms) by the GC (gas chromatography) technique using a hollow capillary column packed with ZYLON fibers (about 580 to 590 filaments).

The chromatogram thus obtained is shown in FIG. 8. The results shown in FIG. 8 clearly indicate that these alkanes (from the alkane having 10 carbon atoms (initial peak) to the alkane having 19 carbon atoms (final peak)) are completely separated.

EXAMPLE 6

This Example is herein given for illustrating an example in which a heptane solution containing dodecane, tetradecane and hexadecane (1% each) is separated by the GC (gas chromatography) technique using a column comprising a hollow capillary of fussed silica having a size of 0.32 mm inner diameter×100 cm long packed with 266 ZYLON fibers having a diameter of 11 μm. The conditions used for the separation are as follows:
Column Temperature: 120° C.;
Injector: splitless (250° C.);
Detection: FID (250° C.);
Column Head Pressure: 200 kPa.

Figure 9:
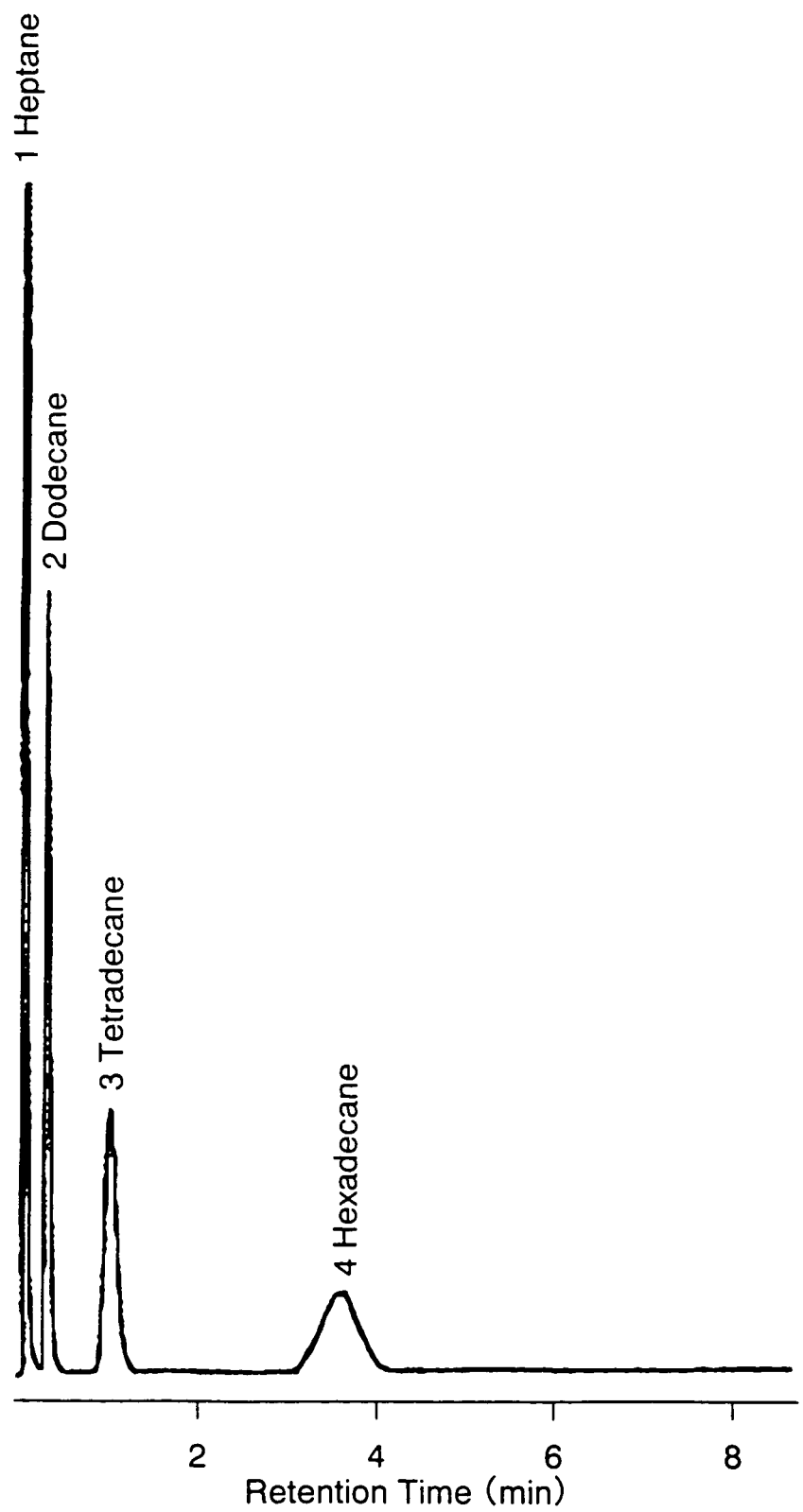
FIG. 9 is a chromatogram showing the results obtained by separating dodecane, tetradecane and hexadecane (a solution in heptane, each having a concentration of 1%) by the GC (gas chromatography) technique using a hollow capillary column packed with ZYLON fibers.

The chromatogram thus obtained is shown in FIG. 9. The separation of each component and the shape of each peak are good.

EXAMPLE 7

Figure 10:
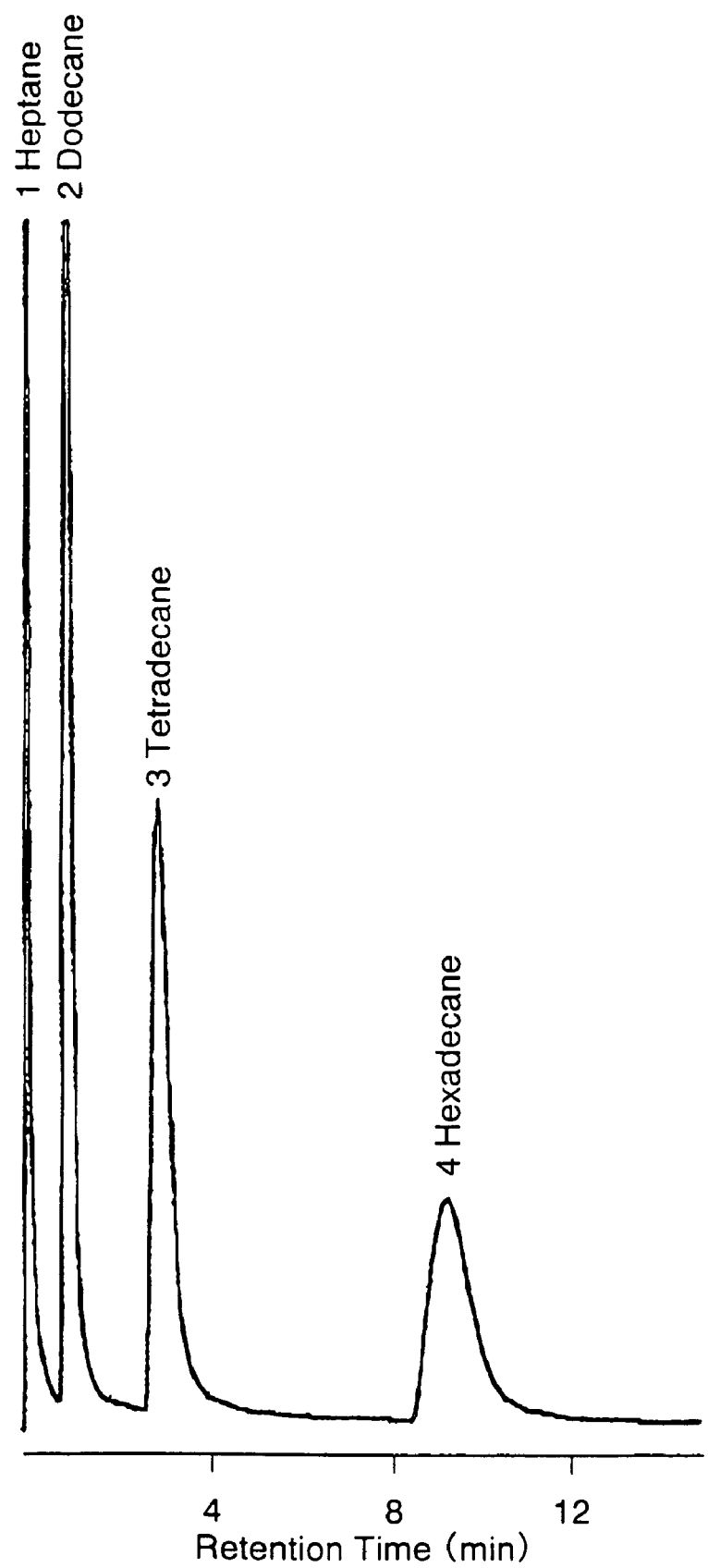
FIG. 10 is a chromatogram showing the results obtained by separating dodecane, tetradecane and hexadecane (a solution in heptane, each having a concentration of 1%) by the GC (gas chromatography) technique using a hollow capillary column packed with ZYLON fibers, which have been subjected to liquid phase coating with silicone oil.

A column comprising a hollow capillary of fussed silica having a size of 0.32 mm inner diameter×100 cm long packed with 266 ZYLON fibers having a diameter of 11 μm, which was identical to that used in Example 6, was washed with water, acetone and chloroform and then aged at 300° C. for 60 hours. The column was then coated with a 5% solution of silicone oil (HR-1 available from Shinwa Chemical Industry Co., Ltd.) in hexane according to the dynamic method at 5 kg/cm$^2$ and further aged at 300° C. for 60 hours. Then a heptane solution containing dodecane, tetradecane and hexadecane (1% each) identical to that used in Example 6 was separated by the GC technique using the foregoing hollow capillary column. The chromatogram thus obtained is shown in FIG. 10. The conditions used for the separation were the same as those used in Example 6.

The results shown in FIG. 10 indicate that the liquid phase coating of the column with silicone oil permits further improvement of the separation of each component and the shape of each peak.

EXAMPLE 8

This Example is herein given for illustrating an example in which three kinds of n-alkyl p-hydroxybenzoates (common name: parabenes) are separated by the CEC (capillary electrochromatography) technique using the separation column for chromatography according to the present invention (a column comprising a hollow capillary of PEEK having an inner diameter of 0.2 mm and packed with 280 Kevlar fibers having a diameter of 11.5 μm; or a column comprising a hollow capillary of PEEK having an inner diameter of 0.2 mm and packed with 280 ZYLON fibers having a diameter of 11.5 μm).

The conditions used for the separation are as follows:
Inner Diameter: 0.2 mm×500 mm; Effective Length: 50 mm;
Mobile Phase: 2.5 mM Tris-HCl Buffer Solution (pH 8.1);
Detection: UV (254 nm);
Applied Voltage: 5 kV.

Figure 11:
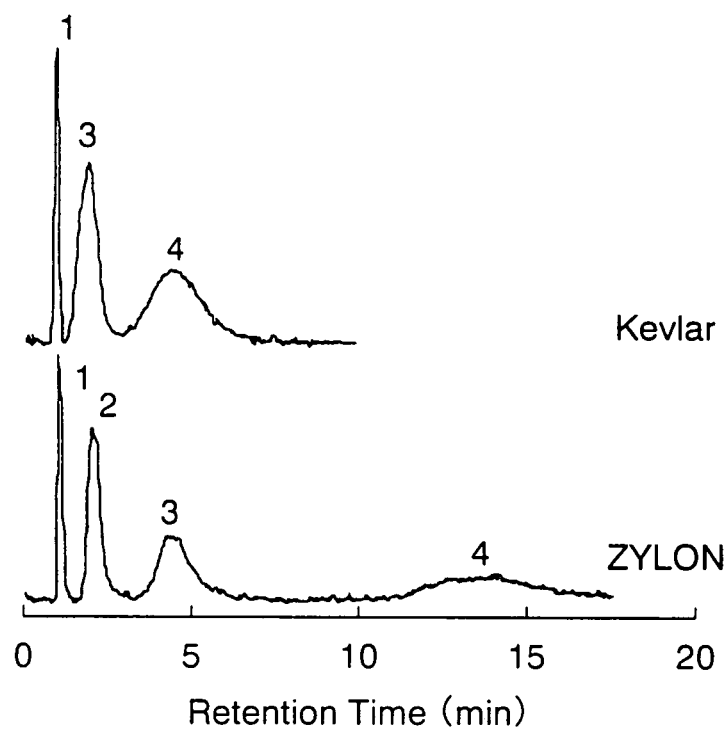
FIG. 11 is a chromatogram showing the results obtained by separating three kinds of n-alkyl p-hydroxybenzoates by the CEC (capillary electrochromatography) technique using a hollow capillary column packed with Kevlar fibers or ZYLON fibers. Peaks 1 to 4 correspond to thiourea, ethyl p-hydroxybenzoate, n-propyl p-hydroxybenzoate and n-butyl p-hydroxybenzoate, respectively.

The chromatogram thus obtained is shown in FIG. 11. In this figure, the peaks 1 to 4 are assigned to thiourea, ethyl p-hydroxybenzoate, n-propyl p-hydroxybenzoate and n-butyl p-hydroxybenzoate, respectively.

EXAMPLE 9

This Example is provided for illustrating an example in which three kinds of n-alkyl p-hydroxybenzoates (common name: parabenes) are separated by the CEC (capillary electrochromatography) technique using the separation column for chromatography according to the present invention (a column comprising a hollow capillary of PEEK having an inner diameter of 0.2 mm and packed with 250 cellulose acetate fibers having a diameter of 12 μm; or a column comprising a hollow capillary of PEEK having an inner diameter of 0.2 mm and packed with 280 ZYLON fibers having a diameter of 11.5 μm). The conditions used for the separation are as follows:
Inner Diameter: 0.2 mm×500 mm; Effective Length: 50 mm;
Mobile Phase: Methanol/Water/50 mM Tris-HCl Buffer Solution (pH 8.2)=50/45/5;
Detection: UV (254 nm);
Applied Voltage: 10 kV, 10 seconds.

Figure 12:
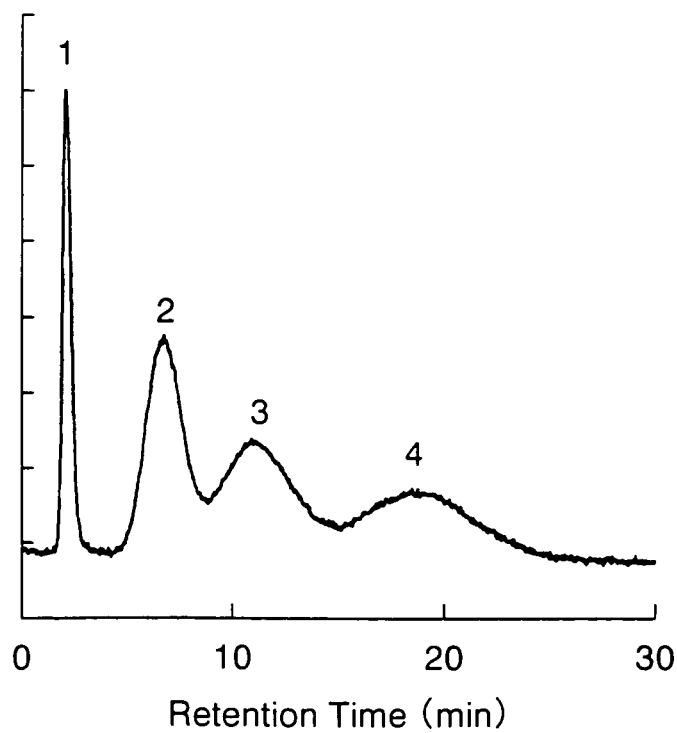
FIG. 12 is a chromatogram showing the results obtained by separating three kinds of n-alkyl p-hydroxybenzoates by the CEC (capillary electrochromatography) technique using a hollow capillary column packed with cellulose acetate fibers. Peaks 1 to 4 correspond to thiourea, methyl p-hydroxybenzoate, n-butyl p-hydroxybenzoate and n-hexyl p-hydroxybenzoate, respectively.

The chromatogram thus obtained is shown in FIG. 12. In this figure, the peaks 1 to 4 are assigned to thiourea, methyl p-hydroxybenzoate, n-butyl p-hydroxybenzoate and n-hexyl p-hydroxybenzoate, respectively.

EXAMPLE 10

This Example is herein provided for illustrating the results obtained by microliquid chromatographic analysis of di-n-butyl phthalate present in a water sample, which has preliminarily been concentrated by the fiber-in-tube SPME technique, while making use of the separation column according to the present invention. The conditions used for the SPME concentration are as follows:
SPME Tube: A PEEK tube (inner diameter 0.50 mm×5 mm) packed with ZYLON fibers (HM Type);
Flow Rate and Time of Extraction: 32 μl/min×15 minutes;
Desorption Solvent: Mobile Phase;
Micro LC Conditions: Column: Develosil ODS-5 (inner diameter 0.53 mm×200 mm);
Mobile Phase: Methanol/Water=95/5 (v/v), 4 μl/min;
Amount of Sample Injected: 0.3 μl; and
Detection: UV (254 nm).

Figure 13:
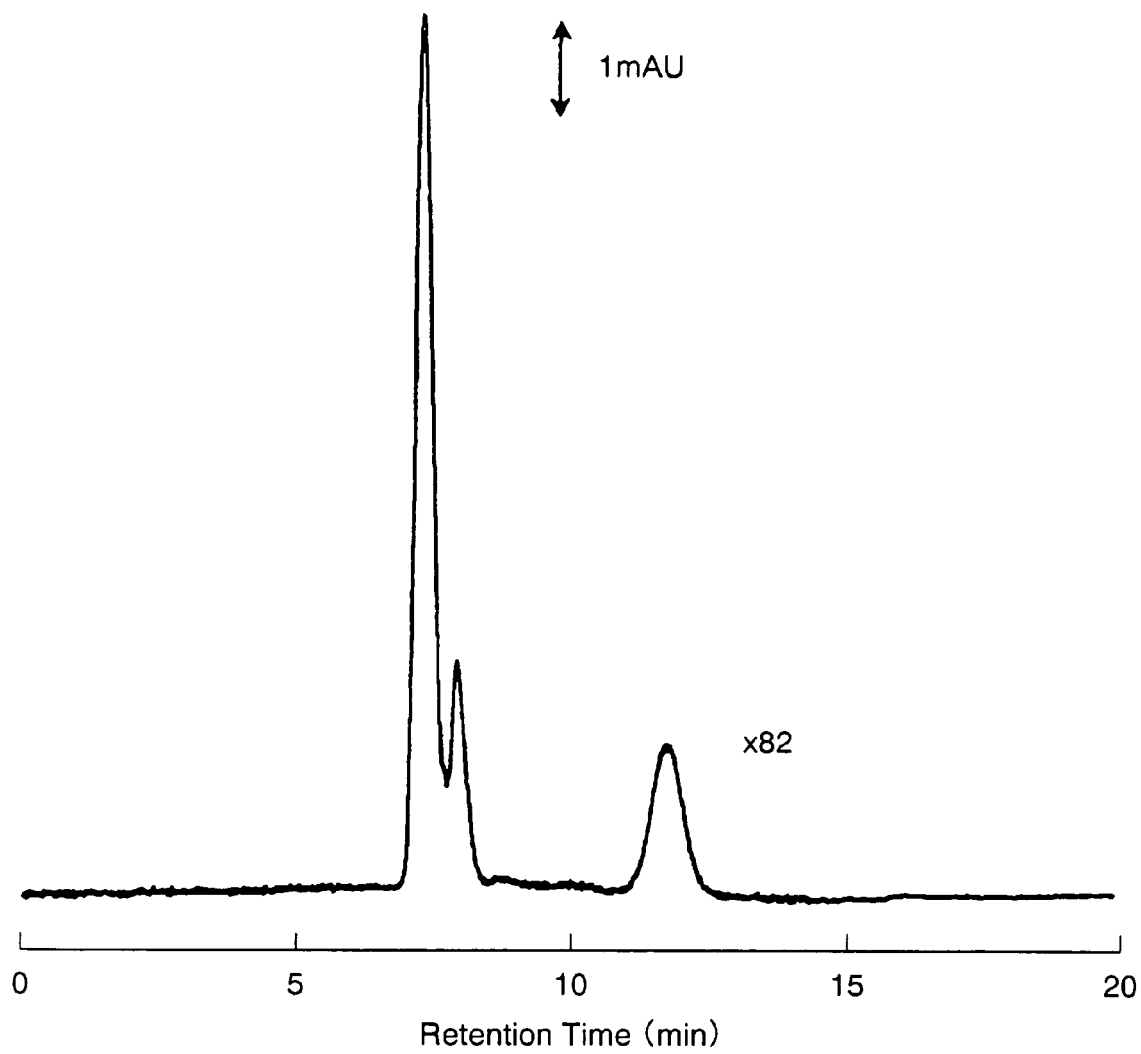
FIG. 13 is a chromatogram showing the results obtained by microcolumn liquid chromatography analysis of di-n-butyl phthalate present in a water sample, which has preliminarily been concentrated by a fiber-in-tube SPME technique.

The chromatogram thus obtained is shown in FIG. 13. In FIG. 13, "×82" means the concentration factor.

EXAMPLE 11

This Example is herein provided for illustrating the results obtained by analyzing di-n-alkyl phthalates by liquid chromatography using the separation column according to the present invention. The conditions used for the chromatography are as follows:
Column: A column (inner diameter 0.25 mm×150 mm) packed with ZYLON fibers (HM Type);
Mobile Phase: Methanol/Water=40/60 (v/v), 4 μl/min; and
Detection: UV (254 nm).

Figure 14:
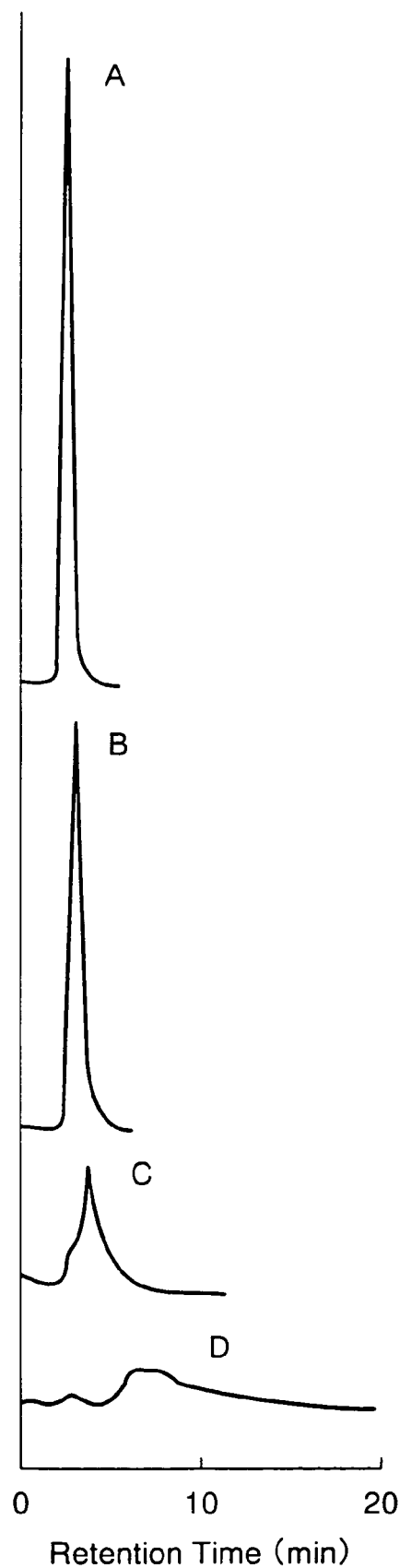
FIG. 14 is a chromatogram showing the results obtained by analyzing di-n-alkyl phthalates by liquid chromatography using a hollow capillary column packed with ZYLON fibers (HM Type). In the chromatogram, peaks A to D correspond to dimethyl phthalate, diethyl phthalate, di-n-propyl phthalate and di-n-butyl phthalate, respectively.

The chromatogram thus obtained is shown in FIG. 14. In this chromatogram, peaks A to D are assigned to dimethyl phthalate, diethyl phthalate, di-n-propyl phthalate and di-n-butyl phthalate, respectively.

EXAMPLE 12

This Example is conducted for showing the results obtained by analyzing naphthalene by the liquid chromatography using the separation column according to the present invention. The conditions used for the chromatography are as follows:
Column: A column (inner diameter 0.25 mm×150 mm) packed with ZYLON fibers (HM Type);
Mobile Phase A: Methanol/Water=50/50 (v/v);
Mobile Phase B: Methanol/Water=40/60 (v/v);
Flow Rate: 4 μl/min;
Detection: UV (254 nm).

Figure 15:
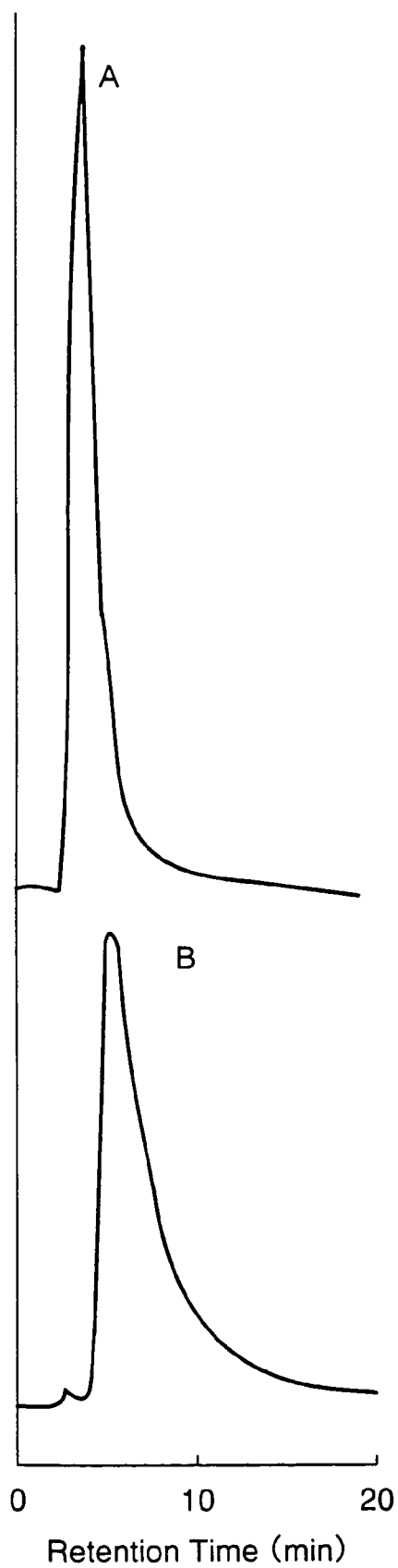
FIG. 15 is a chromatogram showing the results obtained by analyzing naphthalene by the liquid chromatography technique using a hollow capillary column packed with ZYLON fibers (HM Type).

The chromatogram thus obtained is shown in FIG. 15.

EXAMPLE 13

This Example is herein provided for illustrating the results obtained by analyzing pyrene by liquid chromatography using the separation column according to the present invention. The conditions for the chromatography are as follows:
Column: A column (inner diameter 0.25 mm×150 mm) packed with ZYLON fibers (HM Type);

Mobile Phase A: Methanol/Water=80/20 (v/v);
Mobile Phase B: Methanol/Water=70/30 (v/v);
Flow Rate: 4 µl/min; and
Detection: UV (254 nm).

The chromatogram thus obtained is shown in FIG. 16.

The foregoing microcolumn packed with long fibers according to the present invention can be used as an extraction-concentration medium and a separation medium. The use of polymeric long fibers, which have chemical structures specially designed so that they can specifically interact with a target substance (a solute or an analyte) to be analyzed, permits the selective or preferential extraction and/or concentration of the solute. Dyed fibers may likewise be used in such applications with a high probability. This is because the dye molecules are present in the dyed fibers and they may serve as a kind of stationary phase ligand or sites capable of specifically interacting with the solute.

We claimed is:

1. A separation column comprising a hollow capillary and a collected body packed in the hollow capillary,
    wherein the collected body is a stationary phase consisting essentially of long fibers having an adsorbing ability selective towards a target solute and arranged along the axial direction of the capillary,
    wherein the long fibers are aramid fibers,
    having a diameter ranging from 100 nm to 100 µm and a length of from 5 cm to 10 m.

2. The separation column of claim 1, wherein the hollow capillary has an inner diameter ranging from 1 to 600 µm.

3. The separation column of claim 1, wherein the total number of the long fibers packed in the hollow capillary ranges from 10 to 3000.

4. The separation column of claim 1, wherein the long fibers are surface treated fibers or chemically modified fibers.

5. The separation column of claim 1, wherein the stationary phase consists of the long fibers.

6. The separation column of claim 5, wherein the hollow capillary has an outer diameter of from 200 to 600 µm.

7. The separation column of claim 6, wherein the long fibers have a length of from to 10 cm to 10 m.

8. The separation column of claim 6, wherein the long fibers and the hollow capillary have the same length.

9. A solid phase extraction medium comprising a hollow capillary and a collected body packed in the hollow capillary,
    wherein the collected body consists essentially of long fibers having an adsorbing ability selective towards a target solute and arranged along the axial direction of the capillary,
    wherein the long fibers are aramid fibers,
    having a diameter ranging from 100 nm to 100 µm and a length of from 5 cm to 10 m.

10. The solid phase extraction medium of claim 9, wherein the hollow capillary has an inner diameter ranging from 1 to 600 µm.

11. The solid phase extraction medium of claim 9, wherein the total number of the long fibers packed in the hollow capillary ranges from 10 to 3000.

12. The solid phase extraction medium of claim 9, wherein the long fibers are surface treated fibers or chemically modified fibers.

13. The separation column of claim 9, wherein the collected body consists of the long fibers.

14. The separation column of claim 13, wherein the hollow capillary has an outer diameter of from 200 to 600 µm.

15. The separation column of claim 13, wherein the long fibers have a length of from to 10 cm to 10 m.

16. The separation column of claim 13, wherein the long fibers and the hollow capillary have the same length.

* * * * *

UNITED STATES PATENT AND TRADEMARK OFFICE
CERTIFICATE OF CORRECTION

PATENT NO. : 7,211,189 B2 Page 1 of 1
APPLICATION NO. : 10/873206
DATED : May 1, 2007
INVENTOR(S) : Jinno et al.

It is certified that error appears in the above-identified patent and that said Letters Patent is hereby corrected as shown below:

On the title page, Item (54), and at the beginning of column 1, the title is incorrect. Item (54) and the beginning of column 1 should read:

-- (54) SEPARATION COLUMN FOR CHROMATOGRAPHY, MEDIUM FOR SOLID PHASE EXTRACTION AND SAMPLE INJECTION SYSTEM FOR CHROMATOGRAPHY --

Signed and Sealed this

Tenth Day of July, 2007

JON W. DUDAS
*Director of the United States Patent and Trademark Office*